(12) United States Patent
Nunes Nogueira et al.

(10) Patent No.: US 12,421,482 B2
(45) Date of Patent: Sep. 23, 2025

(54) MONITORING SYSTEM FOR WINEMAKING

(71) Applicant: Watgrid, S.A., Ilhavo (PT)

(72) Inventors: Rogério Nunes Nogueira, Gafanha da Boa Hora (PT); Lúcia Maria Botas Bilro, Gafanha da Encarnação (PT); Fábio Patrício Domingues Gonçalves, Pombal (PT); Pedro Miguel Estima da Costa, Aveiro (PT); Ricardo José Ventura de Sousa e Carvalho Pereira, Oporto (PT)

(73) Assignee: Watgrid, S.A. (PT)

( * ) Notice: Subject to any disclaimer, the term of this patent is extended or adjusted under 35 U.S.C. 154(b) by 1094 days.

(21) Appl. No.: 16/686,509

(22) Filed: Nov. 18, 2019

(65) Prior Publication Data

US 2020/0157479 A1     May 21, 2020

Related U.S. Application Data

(60) Provisional application No. 62/769,641, filed on Nov. 20, 2018.

(51) Int. Cl.
*C12M 1/00* (2006.01)
*C12G 1/00* (2019.01)
(Continued)

(52) U.S. Cl.
CPC ............ *C12G 1/00* (2013.01); *C12M 41/12* (2013.01); *C12M 41/26* (2013.01); *C12M 41/30* (2013.01);
(Continued)

(58) Field of Classification Search
CPC .................. C12M 41/12; C12G 1/00
See application file for complete search history.

(56) References Cited

U.S. PATENT DOCUMENTS

| | | |
|---|---|---|
| 4,368,639 A | 1/1983 | Owens |
| 4,984,451 A | 1/1991 | Wilen |

(Continued)

FOREIGN PATENT DOCUMENTS

| | | |
|---|---|---|
| CN | 204214506 | 3/2015 |
| DE | 102007047175 A1 | 4/2009 |

(Continued)

OTHER PUBLICATIONS

Int'l Search Report and Written Opinion Appln No. PCT/IB2019/001236 mailed Apr. 23, 2020.

(Continued)

*Primary Examiner* — Nathan A Bowers
(74) *Attorney, Agent, or Firm* — McAndrews, Held & Malloy, Ltd.

(57) ABSTRACT

Aspects of a monitoring method and system for winemaking are provided. The system comprises at least two sensors, a controller, a wireless transmitter and a wireless receiver. One sensor measures a wine parameter, while the other sensor measures an ambient condition. The controller is able to generate an alarm based on the wine parameter and the ambient condition. The wireless transmitter is able to communicate the wine parameter and the ambient condition to a remote database. The wireless receiver is able to receive a modification to the firmware.

20 Claims, 2 Drawing Sheets

(51) Int. Cl.
*C12M 1/34* (2006.01)
*G01S 19/00* (2010.01)
*G01S 19/01* (2010.01)
*G08B 21/18* (2006.01)

(52) U.S. Cl.
CPC ............ *C12M 41/40* (2013.01); *C12M 41/44* (2013.01); *G01S 19/01* (2013.01); *G08B 21/182* (2013.01)

(56) References Cited

U.S. PATENT DOCUMENTS

| | | | |
|---|---|---|---|
| 5,603,220 A * | 2/1997 | Seaman | A61J 1/165 |
| | | | 62/3.62 |
| 5,953,954 A | 9/1999 | Drain | |
| 2004/0076946 A1 | 4/2004 | Trauner | |
| 2006/0113374 A1 | 6/2006 | Taylor et al. | |
| 2010/0120139 A1 * | 5/2010 | Busujima | C12M 41/34 |
| | | | 435/303.2 |
| 2014/0081580 A1 | 3/2014 | Kim et al. | |
| 2014/0200840 A1 | 7/2014 | Cox et al. | |
| 2015/0144300 A1 * | 5/2015 | Parker | G05D 23/1919 |
| | | | 165/61 |
| 2015/0198474 A1 | 7/2015 | Howard | |
| 2015/0253174 A1 | 9/2015 | Barrett et al. | |
| 2017/0107476 A1 * | 4/2017 | Polley | G01N 30/8637 |
| 2017/0217027 A1 * | 8/2017 | Boucard | B01L 9/523 |
| 2017/0253848 A1 * | 9/2017 | Emmerson | C12Q 3/00 |
| 2017/0283760 A1 * | 10/2017 | Peng | C12M 41/42 |
| 2018/0136020 A1 | 5/2018 | Sweet | |
| 2019/0040347 A1 * | 2/2019 | Kim | C12M 47/02 |
| 2020/0071655 A1 * | 3/2020 | Palmaz | C12M 41/26 |
| 2021/0108169 A1 * | 4/2021 | Petersen | C12M 41/42 |
| 2021/0140809 A1 * | 5/2021 | Vernekar | G01F 23/804 |
| 2022/0041973 A1 * | 2/2022 | Stine | C12M 41/48 |

FOREIGN PATENT DOCUMENTS

| | | |
|---|---|---|
| EP | 1270716 | 1/2003 |
| WO | 2013028144 A3 | 2/2013 |
| WO | 2017216746 A1 | 12/2017 |

OTHER PUBLICATIONS

Int'l Search Report and Written Opinion Appln No. PCT/IB2017/053549 mailed Oct. 5, 2017 (6 pgs).
N. Oliveiram et al., Winegrid®: the remote and real-time wine production process monitoring system (6 pgs).
Portuguese Search Report Appln No. 109451 dated Nov. 18, 2016 (2 pgs).
Int'l Preliminary Report on Patentability Appln No. PCT/IB2019/001236 mailed Jun. 3, 2021.
Australian Examination Report No. 3 Appln No. 2019383774 dated Mar. 15, 2023.
Australian Examination Report No. 1 Appln No. 2019383774 dated Apr. 12, 2022.
Australian Examination Report No. 2 Appln No. 2019383774 dated Jan. 10, 2023.
Why and How To Use Switching Voltage Regulators To Maintain a Constant Voltage Level [retrieved from internet on Jan. 10, 2023] < URL: https://web.archive.org/web/20211206114217 /https://www.intorobotics.com/why-and-how-to-use-switchingvoltage-regulators-to-maintain-a-constant-voltage-level/ > Published on Feb. 14, 2017.
Intro to Electronic Components: Voltage Regulators and DC Converters [retrieved from internet on Jan. 10, 2023] < URL: https://maker.pro/custom/tutorial/intro-to-electronic-components-voltage-regulatorsand-dc-converters > Published on Oct. 17, 2018.
Australian Examination Report No. 4 Appln No. 2019383774 dated Apr. 12, 2023.
Australian Examination Report No. 2 Appln No. 2023202268 dated Sep. 5, 2024.

* cited by examiner

MONITORING SYSTEM FOR WINEMAKING

PRIORITY CLAIM

This patent application claims the benefit of priority to U.S. provisional patent application 62/769,641, titled "Monitoring System for Winemaking," filed on Nov. 20, 2018. The above referenced document is hereby incorporated herein by reference in its entirety.

BACKGROUND

Limitations and disadvantages of conventional and traditional monitoring systems for winemaking will become apparent to one of skill in the art, through comparison of such systems with some aspects of the present invention as set forth in the remainder of the present application with reference to the drawings.

BRIEF SUMMARY OF THE INVENTION

Monitoring systems for winemaking substantially as shown in and/or described in connection with at least one of the figures, as set forth more completely in the claims. These and other advantages, aspects and novel features of the present invention, as well as details of an illustrated embodiment thereof, will be more fully understood from the following description and drawings.

DETAILED DESCRIPTION OF THE INVENTION

This disclosure describes systems for monitoring winemaking or other similar processes, for example. Many facets of wine change during the processes of maceration, fermentation and maturation. Parameters (e.g., pressure, temperature, density, level, turbidity, color, pH, alcohol content) may be automatically captured continuously or otherwise over time and wirelessly transferred to a database for analysis and storage. Thresholds may be set such that a winemaker can be notified when the monitored parameters are out of a selected or desired range.

Figure 1:
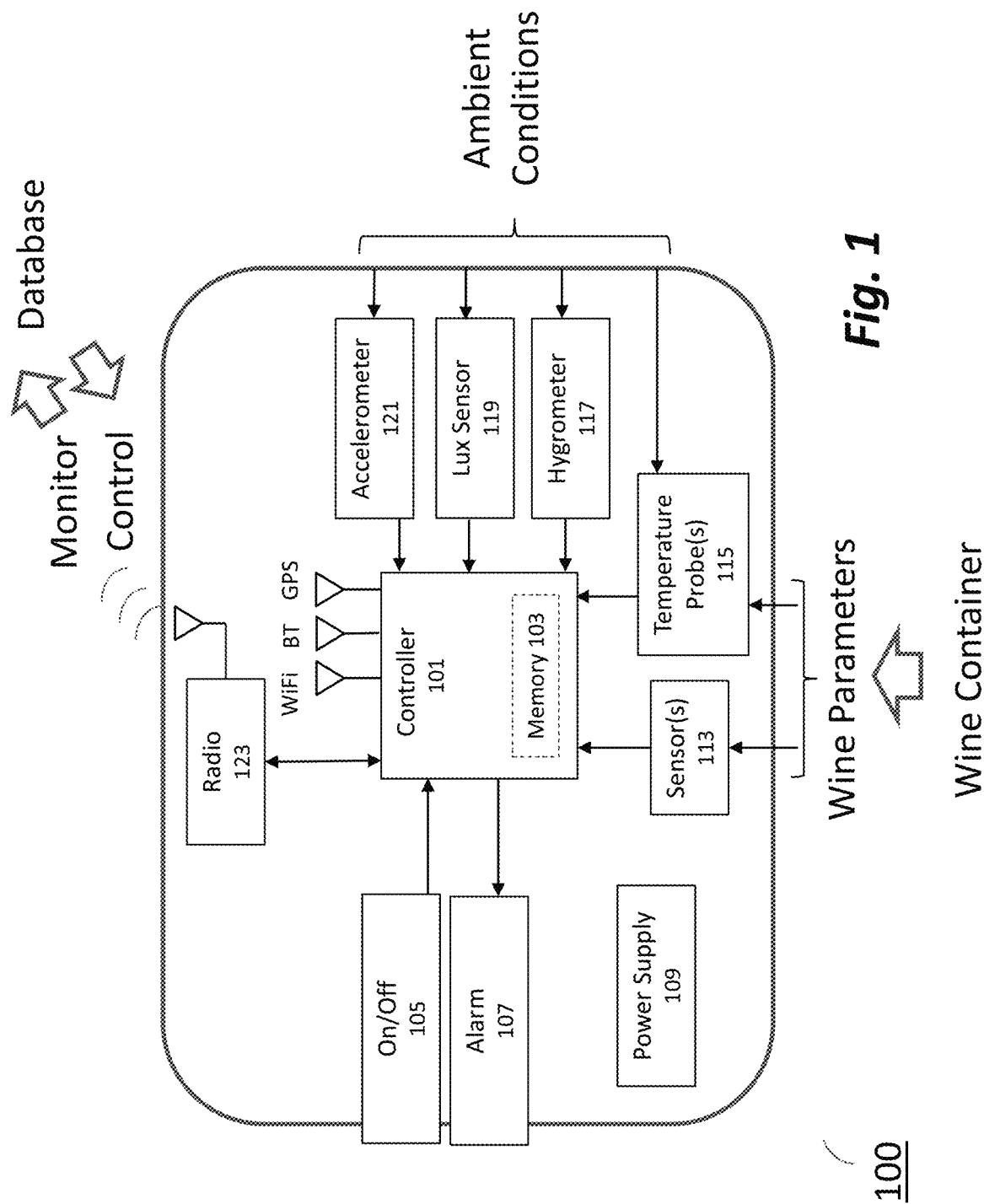
FIG. 1 illustrates components of a sensor device in accordance with an example implementation of this disclosure.

FIG. 1 illustrates components of a sensor device in accordance with an example implementation of this disclosure. The depicted components of the sensor device 100 include a controller 101, memory 103, an on/off controller 105, an alarm 102, a power supply 109, one or more sensor(s) 113, a temperature probe 115, a hygrometer 117, a lux sensor 119, an accelerometer 121 and a wireless communication module (e.g., WiFi, Bluetooth, or LoRA radio 123).

In operation, in a winemaking example, the sensor device 100 is coupled to a wine barrel or vat during a winemaking process. The temperature probe 115 measures the temperature of the wine, and the one or more sensor(s) 113 measure additional parameters (e.g., pressure, density, level, turbidity, color, pH, alcohol content) of the wine. These measurements are conveyed to the controller 101, which is operable to control a wireless transmission of the information to a database for analysis and storage.

The controller 101 may be operable to derive certain parameters from those supplied by the one or more sensor(s) 113. For example, a wine level and/or density may be derived according to a pressure measurement. The controller 101 may be operable to monitor the power level provided by the power supply 109. If the power supply 109 comprises one or more batteries, for example, the controller 101 may be operable to monitor and report to the database when the batteries should be replaced or recharged. Alternatively, an additional circuit in the power supply 109 may monitor the batteries and convey a low power indication to the controller 101.

The controller 101 may comprise memory 103 for data back-up in the event of power failure or the interruption of wireless communication. Alternatively, the memory 103 may reside external to the controller 101. The memory 103 may be Flash, and may also reside on a removable Flash card.

The on/off controller 105 may comprise a user-controlled button. Pressing the button 105 ON can trigger the sensor device 100 to send a beacon to enable pairing with a network. Pressing the button 105 OFF can trigger the sensor device 100 to store all current information in a Flash card before powering down.

The sensor device 100 may generate local alarms that may be customized by the winemaker or other user. The alarm 107 may convey a visual and/or an audio alarm 107. Different sounds and/or different colors may indicate various conditions. By way of example and without limitation, a flashing red light or a beeping may indicate a low battery. A solid yellow light may indicate a low wine level and a need for topping off the wine. A solid blue light may indicate that the wine is below a low temperature threshold. Of course, other example conditions can be indicated by various sounds and/or colors using the visual and/or an audio alarm 107. The alarm 107 may comprise an LED. Such an LED may be incorporated into an on/off button 105. The alarm 107 may also be used to indicate the status of a pairing of the sensor device 100 to a local network.

The one or more sensor(s) 113 and the temperature probe 115 are operably coupled to a wine container, such as a barrel or a vat. The type of sensors used may depend of the current stage of winemaking. During fermentation, for example, multiple pressure sensors may be used to measure a change in density and level. The change in pressure may be used by the controller 101 to determine wine density. Alternatively, multiple pressure measurements may be transmitted via the wireless network to the database (e.g., cloud storage). Analysis of this information in the database may be performed by a remote device on the network.

Ambient conditions may also be measured in addition to parameters of the actual wine. A temperature probe 115, a hygrometer 117 and/or a lux sensor 119 may be positioned to measure the conditions around a wine barrel or wine vat. The ambient conditions may also be transmitted via the wireless network to the database.

An accelerometer 121 may indicate the movement of the sensor device 100 and/or the movement of the wine barrel being monitored. Some monitors, for example, require a precise vertical or horizontal orientation. The accelerometer 121 may be used for initial calibration of the orientation as well as for a remote indication that an adjustment is required. The alarm 107 may also be operable to indicate when the sensor device 100 is askew according to the accelerometer 121.

The transceiver may use any wireless communication protocol, such as Bluetooth, WiFi, LoRa or any cellular standard. The LoRa radio 123 may operate according to a Low Power, Wide Area (LPWA) networking protocol designed to wirelessly connect battery operated 'things' to the internet in regional, national or global networks. The LoRa radio 123 may provide key Internet of Things (IoT) requirements such as bi-directional communication, end-to-end security, mobility and localization services. A network architecture may be deployed, for example, in a peer-to-peer and/or star-of-stars topology in which gateways with one or more access points relay messages between end-devices and a central network server. The gateways are connected to a network server via IP connections and act as a transparent bridge, converting RF packets to IP packets and vice versa. The wireless communication may use the Long Range characteristics of the LoRa physical layer, allowing a single-hop link between the end-device and one or many gateways. The LoRa radio 123 may also enable Firmware Over-The-Air (FOTA) upgrades and mass distribution messages to a plurality of sensor devices 100. While FIG. 1 illustrates a LoRA radio, this disclosure also envisions other similar wireless technologies.

The controller 101 may be operable to receive GPS signals for locating the sensor device 100, thereby providing an indoor position system.

Figure 2:
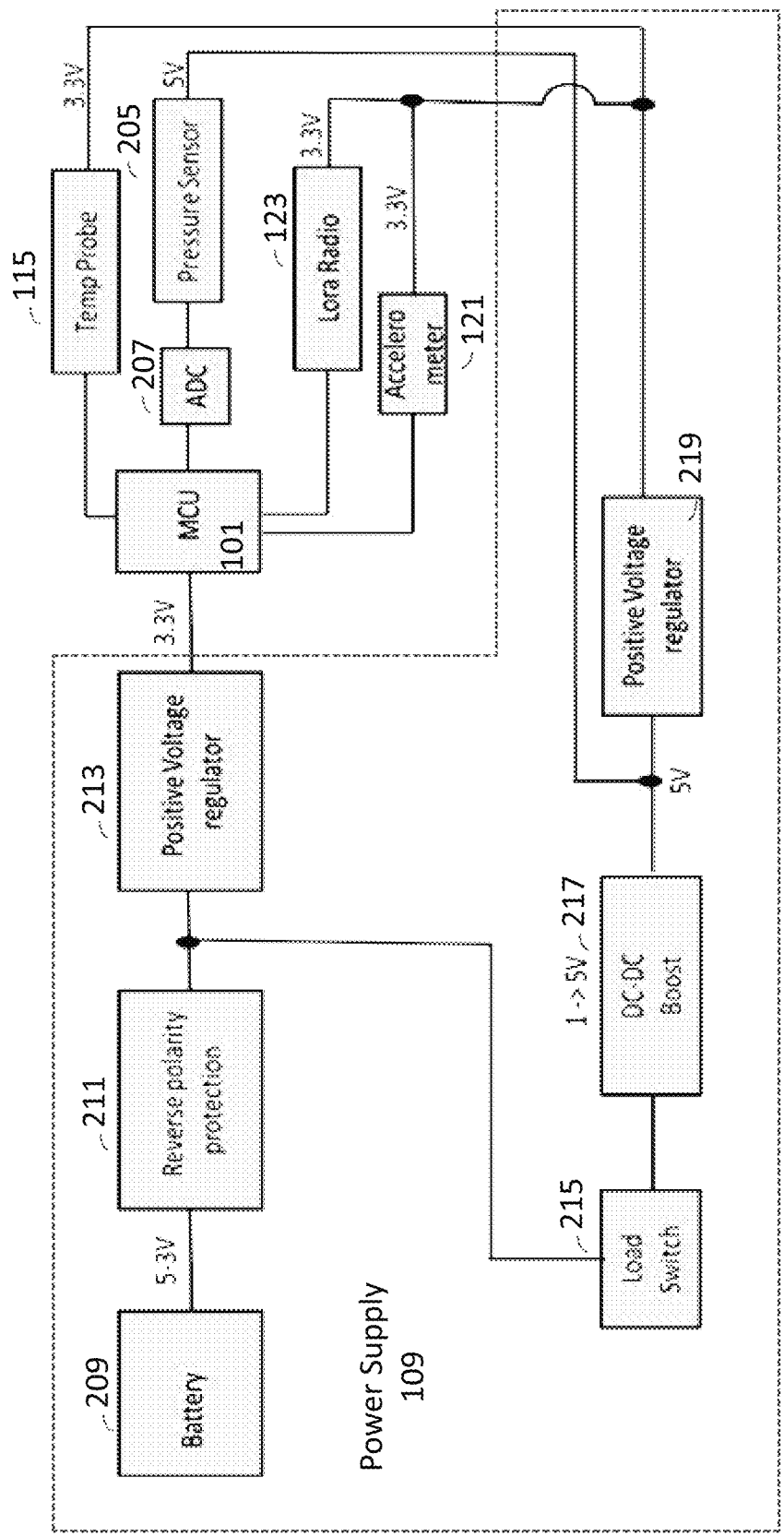
FIG. 2 illustrates components of an alternative sensor device in accordance with an example implementation of this disclosure.

FIG. 2 illustrates components of an alternative sensor device in accordance with an example implementation of this disclosure. As depicted in FIG. 2, a pressure sensor 205 generates an analog signal that is converted to a digital controller input by ADC 207.

The power supply 109 in FIG. 2 generates one or more different voltage levels (e.g., 3.3V and 5V DC) for the circuitry of the sensor device 100. A battery 209 is coupled to a reverse polarity protection circuit 211 to ensure that the battery 209 is installed correctly. A positive voltage regulator 213 coupled to the reverse polarity protection circuit 211 provides power to the controller 101. A load switch 215 is also coupled to the reverse polarity protection circuit 211. The output of the load switch 215 is boosted. For example, a DC-DC boost circuit 217 may be used if an increase of the voltage level is needed. A second positive voltage regulator 219 is coupled to the DC-DC boost circuit 217 to provide 3.3V. The voltage regulator 219 may be used to automatically maintain a constant voltage level. The temperature probe 115, radio module 123 and accelerometer 121 (as described regarding FIG. 1) are driven by a determined voltage level.

A system for monitoring winemaking (e.g., 100 in FIG. 1) comprises at least two sensors (e.g., 113, 115, 117, 119 and/or 121), a controller (e.g., 101), and a radio (e.g., 123) that operates as a wireless transmitter and a wireless receiver. A first sensor (e.g., 113 or 115) measures a wine parameter, while a second sensor (e.g., 117, 119 or 121) measures an ambient condition. The controller (e.g., 101) is able to generate an alarm based on the wine parameter and the ambient condition. The controller (e.g., 101) is also able to trigger an actuator such as a temperature regulation system, a microxygenation system and/or a pump system. The wireless radio transmitter (e.g., 123) is able to communicate the wine parameter, the ambient condition and/or the actuator trigger to a remote database. The wireless receiver (e.g., 123) is able to receive a modification to the firmware.

The wine parameter measured by the first sensor (e.g., 115) may be the temperature of the wine. The wine parameter measured by the first sensor (e.g., 113) may also be pressure, density, level, turbidity, color, pH or alcohol content of the wine. The ambient temperature may be measured by a temperature probe (e.g., 115) that is external to the container of wine. The ambient humidity may be measured by a hygrometer (e.g., 117). The ambient infrared, full-spectrum or human-visible light may be measured by a lux sensor (e.g., 119). The static and dynamic acceleration forces on the system (and by association on the wine container) may be measured by an accelerometer (e.g., 119). For example, the accelerometer (e.g., 119) is able to calibrate an orientation of the system and indicate to a remote device that the system is askew. Also, the accelerometer (e.g., 119) is able to detect sudden motion, such as a movement of the wine container.

The controller (e.g., 101) of the system is able to receive a GPS signal from the radio receiver (e.g., 121) to provide a position of the system. The controller (e.g., 101) is also able to monitor a power supply (e.g., 109) of the system. If the system is battery operated, power supply (e.g., 109) monitoring will notify a winemaker when the battery needs changed or recharged.

The aforementioned system (e.g., 100 in FIG. 1) also enables a winemaker to monitor the winemaking remotely. Such a monitoring method comprises measuring the wine parameter with the first sensor (e.g., 113 or 115); measuring the ambient condition with the second sensor (e.g., 117, 119 or 121); and communicating the wine parameter and the ambient condition to a remote database (e.g., cloud storage) using the wireless radio (e.g., 123). Initial calibration of the system orientation is made possible by the accelerometer (e.g., 121).

The winemaker may also wirelessly upgrade the controller (e.g., 101) via firmware updates sent wirelessly by way of the wireless radio (e.g., 123). One of the components of the controller system 101 may be microcontroller. The firmware upgrade may be made to the controller as a whole or to the microcontroller specifically. The winemaker may also program the controller firmware to activate one or more alarms (e.g., 123) based on the wine parameters and/or the ambient conditions. For example, the alarm (e.g., 123) could be a red light if the batter is low or a yellow light if the wine container is tilted. Furthermore, the alarm 123 may be customized by the winemaker or other user via remote user interface The alarm (e.g., 123) could also enable an audible sound, such as a tone, multi-tone, or verbal alert if the wine parameters and/or the ambient conditions are outside of preprogrammed ranges.

As utilized herein the terms "circuits" and "circuitry" refer to physical electronic components (i.e. hardware) and any software and/or firmware ("code") which may configure the hardware, be executed by the hardware, and or otherwise be associated with the hardware. As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

The present invention may be realized in hardware, software, or a combination of hardware and software. The present invention may be realized in a centralized fashion in at least one computing system or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

The present invention may be realized in a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

While the present invention has been described with reference to certain embodiments, it will be understood by those skilled in the art that various changes may be made and equivalents may be substituted without departing from the scope of the present invention. Those skilled in the art will understand that, in addition to winemaking, the present invention may be used for making of other products (e.g., whiskey, cognac, brandy, rum, gin, vodka, tequila, beer) without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A system for monitoring winemaking comprising:
   a first sensor operable to measure a wine parameter, wherein the first sensor is powered via a first voltage regulator;
   a second sensor operable to measure an ambient condition;
   a controller operable according to firmware stored in a memory, wherein:
      the memory resides on a removable Flash card,
      the controller is operable to generate an alarm according to the wine parameter and the ambient condition, and
      the controller is powered via a second voltage regulator;
   a wireless transmitter operable to communicate the wine parameter and the ambient condition to a remote database; and
   a wireless receiver operable to receive a modification to the firmware.

2. The system according to claim 1, wherein the wine parameter is one of a pressure, a temperature, a density, a level, a turbidity, a color, a pH and an alcohol content.

3. The system according to claim 1, wherein the ambient condition is measured by a temperature probe that is external to a container that comprises the wine.

4. The system according to claim 1, wherein the ambient condition is measured by a hygrometer.

5. The system according to claim 1, wherein the ambient condition is measured by a lux sensor.

6. The system according to claim 1, wherein the system comprises an accelerometer.

7. The system according to claim 6, wherein the accelerometer is operable to calibrate an orientation of the system.

8. The system according to claim 6, wherein the accelerometer is operable to remotely indicate that the system is askew.

9. The system according to claim 1, wherein the controller is operable to receive a GPS signal to provide a position of the system.

10. The system according to claim 1, wherein the controller is operable to monitor a power supply of the system.

11. A method for monitoring winemaking comprising:
   measuring a wine parameter with a first sensor, wherein the first sensor is powered via a first voltage regulator;
   measuring an ambient condition with a second sensor;
   wirelessly upgrading firmware of a controller, wherein:
      the firmware stored on a removable Flash card, and
      the controller is powered via a second voltage regulator;
   generating an alarm according to the wine parameter, the ambient condition and the controller firmware; and
   communicating the wine parameter and the ambient condition to a remote database.

12. The method according to claim 11, wherein the wine parameter is one of a pressure, a temperature, a density, a level, a turbidity, a color, a pH and an alcohol content.

13. The method according to claim 11, wherein the ambient condition is measured by a temperature probe that is external to a container that comprises the wine.

14. The method according to claim 11, wherein the ambient condition is measured by a hygrometer.

15. The method according to claim 11, wherein the ambient condition is measured by a lux sensor.

16. The method according to claim 11, wherein the remote database is a cloud storage.

17. The method according to claim 11, wherein the method comprises calibrating an orientation of the system using an accelerometer.

18. The method according to claim 11, wherein the method comprises remotely indicating that the system is askew according to an accelerometer.

19. The method according to claim 11, wherein the method comprises receiving a GPS signal to provide a position of the system.

20. The method according to claim 11, wherein the method comprises monitoring a power supply of the system.

* * * * *